United States Patent
Arango

(10) Patent No.: US 7,078,024 B2
(45) Date of Patent: Jul. 18, 2006

(54) COMPOSITIONS AND METHOD FOR PROMOTING THE GROWTH OF HUMAN HAIR

(76) Inventor: Amparo Arango, 1550 NE 123rd St., Building "N"—Apt. 407, North Miami, FL (US) 33161

( * ) Notice: Subject to any disclaimer, the term of this patent is extended or adjusted under 35 U.S.C. 154(b) by 0 days.

(21) Appl. No.: 10/455,520

(22) Filed: Jun. 4, 2003

(65) Prior Publication Data

US 2004/0247554 A1    Dec. 9, 2004

(51) Int. Cl.
*A61Q 7/00* (2006.01)
*A61K 8/00* (2006.01)
*A61K 8/18* (2006.01)

(52) U.S. Cl. .................. 424/70.1; 424/94.65; 424/401; 435/212; 435/195

(58) Field of Classification Search ................. 424/401, 424/70.1, 94.65; 435/183, 195, 212
See application file for complete search history.

(56) References Cited

U.S. PATENT DOCUMENTS

| | | | | |
|---|---|---|---|---|
| 4,999,187 A | * | 3/1991 | Vernon | 424/705 |
| 5,665,338 A | * | 9/1997 | Tanimura et al. | 424/70.51 |
| 5,738,879 A | * | 4/1998 | Rine | 424/708 |
| 6,350,582 B1 | * | 2/2002 | Baumgartner | 435/7.1 |

* cited by examiner

*Primary Examiner*—Ruth A. Davis
(74) *Attorney, Agent, or Firm*—Ruben Alcoba, Esq.; Laurence Edson, Esq.

(57) ABSTRACT

Provided are compositions comprising monoethanolamine salts of thioglycolic, salicylic, lactic and glycolic acids in combination with an organic enzyme, preferably papain, and an oxidizing aged their methods of use to induce hair growth in the scalp of humans and other mammals.

7 Claims, No Drawings

COMPOSITIONS AND METHOD FOR PROMOTING THE GROWTH OF HUMAN HAIR

TECHNICAL FIELD

This invention relates generally to compositions and methods directed at promoting the growth of hair in men and women and other mammals. Specifically, this invention is directed at compositions comprising monoethanolamine salts of thioglycolic, salicylic, lactic and glycolic acids in combination with an enzyme, preferably papain, with an oxidizing agent, and their methods of use to induce hair growth in the scalp of humans and other mammals.

BACKGROUND OF THE INVENTION

The average male or female scalp is endowed with between 100,000 and 150,000 hair follicles from which human hairs are generated. Generally, adult human hair can be divided into two categories, "vellous" and "terminal" hair. Vellous hair is comprised of very thin short hairs, only a centimeter or two long, that contain little or no pigment. The follicles that produce vellous hair do not have oil glands (often called sebaceous glands), and never produce any other kind of hair. Terminal hair is comprised of the long hairs that grow on the head and in many people on the body, arms and legs too. They are produced by follicles with sebaceous glands. In people who have inherited a tendency to baldness the hairs in these follicles gradually become thinner and shorter until they look like vellous hairs.

The human hair growth cycle is essentially composed of three stages which repeats indefinitely in healthy follicles. The three known growth stages which have been identified are: (a) the anagen stage, during which the hair grows, (b) the katagen stage, during which the hair follicle prepares for the next phase, the telogen, and the previously growing hair is converted into a resting hair or club hair and (c) the telogen, which is the resting phase during which hair growth ceases completely. Using a mechanism, not yet fully understood, at some point at the end of the cycle, telogenic follicles commence forming new anagens, causing new hair to grow and existing hair to fall out. This growth cycle repeats itself unchanged during the life of the follicle and is essentially identical for vellous or terminal hair-producing follicles.

It has been determined through observation and experimentation that in order for abundant hair growth to occur, healthy follicles and a good supply for it of all necessary nutrients are required. Unhealthy follicles, such as caused by disease or stress, or improper nutrition can thus result in loss of hair. Hair loss brought about by these factors, however, is usually temporary and can be reversed by eliminating the unhealthy conditions. Such reversible conditions, generally of unknown origin, should not be confused with the more chronic conditions which cause irreversible hair loss by replacing terminal hair with vellous hair and eventually no hair.

The exact pathogenic or genetic mechanism that triggers the shift in certain follicles from producing terminal to vellous, and eventually to a complete absence of, hair, is the subject of much debate. Suffice it to say that there is no consensus among those skilled in the art as to the causes of hair loss in men and women. As a result, numerous attempts have been made to provide methods and/or compositions which effectively, and without adverse consequences, can prevent or reverse the seemingly permanent shift from terminal to vellous hair-producing follicles in certain persons.

However, none of these attempts have proven satisfactory from the standpoint of efficacy, convenience, safety or cost. Accordingly, there is a present need for a convenient, inexpensive, safe and efficient compound to treat persons suffering from hair loss conditions, such as alopecia.

SUMMARY OF THE INVENTION

The subject invention resolves the above-described needs and problems by providing an easy to produce, inexpensive and effective compositions, and method of using same, for the treatment of premature hair loss in adult men and women.

The compositions of the present invention comprises two separate products. The first product is keratin reducing compound comprising a combination of salts, preferably monoethanolamine salts, of thioglycolic, salicylic, lactic and glycolic acids with an enzyme, preferably papain. The second product is an oxidizing compound which restores keratin in hair to its state before application of the first product.

In its preferred embodiment, the present invention relies on the unexpected and beneficial reaction between four salts, an enzyme and sunlight to eliminate the obstacles that block hair growth in the human scalp. It is believed that ultraviolet-B ("UV-B") radiation present in sunlight augments and stimulates the growth of epithelial cells and sebaceous glands which surround human hair follicles resulting in stimulation of the dermal papilla and, consequently, in hair growth.

It is commonly believed that alopecia is caused by a pathological dystrophy of hair follicles which eventually results in their eventual death and replacement by connective fatty tissue. What is required to reverse this pathology are chemical compounds that eliminate excess fatty deposits found in the follicle and surrounding areas of the epidermis.

The four salts employed in the invention are:
Monoethanolamine thioglycolate,
Monoethanolamine salicylate,
Monoethanolamine lactate, and
Monoethanolamine glycolate.

The enzyme utilized in the preferred embodiment is papain. It is believed that the effect of eliminating the hair-loss inducing connective fatty tissue is achieved by the monoethanolamine salts through the elimination of disulfuric bonds present in the keratin amino-acid cystine. Keratin is the essential component of hair, consequently, of the hair follicle root. Cystine is broken down by the monoethanolamine salts into cysteine, which is the reduced state of keratin. After the damaging cells are removed, through a process of oxidation, the disulfuric bonds are reestablished, returning the hair keratin to its original state. The detergent characteristics of monoethanolamine help carry the removed cells safely away from the follicle which in turn stimulates growth of the follicle. The papain enzyme imparts elasticity over the keratin and skin tissues to ease the elimination of pathogenic cells.

Having re-activated the previously dormant hair follicles, and provided said follicles are located in areas where blood circulation is sufficient to deliver required nutrients, hair growth is immediately stimulated and anagenic hair can be seen to develop within a matter of hours after treatment.

The compositions of the present invention have been observed to induce significant long-term hair growth in areas of scalp which were previously devoid, or nearly devoid, of terminal hairs. Such effect has been observed after treatment of the scalp for periods of less than 60 minutes, and with such treatments occurring once every 3 to 12 months. These beneficial results have been achieved without any significant adverse health effects.

Accordingly, it is an object of the present invention to provide a convenient, inexpensive, safe and efficient compound to treat persons suffering from hair loss conditions, such as alopecia.

These and other objects, features, and advantages of the present invention may be more clearly understood and appreciated from a review of ensuing detailed description of the preferred and alternate embodiments and by reference to the accompanying drawings and claims.

DETAILED DESCRIPTION OF THE PREFERRED EMBODIMENT

In its preferred embodiment, the present invention consists of two (2) products which are applied separately and sequentially to the human scalp during a treatment session. The two products are a Monoethanolamine Salt Product and an Oxidizing Agent.

I. Monoethanolamine Salt Product

The Monoethanolamine Salt Product is composed of five (5) primary components. These components, hereafter labeled compounds "A" through "E" respectively, are:

Monoethanolamine salicylate;
Monoethanolamine lactate;
Monoethanolamine glycolate;
Papain; and
Monoethanolamine thioglycolate.

Detailed instructions for the preparation of Compounds "A" through "E" follow.

Compound "A"—Monoethanolamine Salicylate

In a 100 ml glass, heat 50 g of ethyl alcohol ($C_{16}H_{34}O$) to 40° C. and maintain temperature. Slowly add, while stirring, 5 g of salicylic acid ($C_7H_6O_3$) until dissolved. Add 2 g of monoethanolamine ($C_2H_7NO$) until completely mixed. Repeat above process of sequentially adding salicylic acid and monoethanolamine until a total of 20 g of salicylic acid and 8 g of monoethanolamine have been added. Remove heat source and allow to cool. After cooling, test pH of the compound. If pH is not equal to 7.0, slowly add monethanolamine until pH is equal to 7.0.

Compound "B"—Monoethanolamine Lactate

In a 100 ml glass, heat 50 g of distilled water to 40° C. and maintain temperature. Add 18 g of lactic acid ($C_3H_6O_3$). Test pH and slowly add monoethanolamine ($C_2H_7NO$) until a pH of 7.0 is achieved.

Compound "C"—Monoethanolamine Glycolate

In a 100 ml glass, heat 50 g of distilled water to 40° C. and maintain temperature. Add 10 g of glycolic acid ($C_2H_4O_3$). Test pH and slowly add monoethanolamine ($C_2H_7NO$) until a pH of 7.0 is achieved.

Compound "D"—Papain

In a 100 ml glass, combine 50 g of a solution of 30% ethanol ($C_2H_6O$) and distilled water. Slowly dilute 5 g pure papain until well mixed.

Compound "E"—Monoethanolamine Thioglycolate

Compound "E" can be prepared by mixing one of two distinct formulations with sodium bromate ($NaBrO_3$). The two formulations are prepared as follows:

Formulation 1

Place a 200 ml glass in an ice bath and add 26.0 g of distilled water. It is important to determine the purity level of the water. If iron or other metals commonly found in water, are present or suspected, a sequestrant, such as ethylenediaminetetraacetic (EDTA) acid disodium salt ($C_{10}H_{14}N_2Na_2O_8.2H_2O$) should be added, in a quantity not exceeding a final concentration of 0.5%. Add 10 g of thioglycolic acid ($C_2H_4O_2S$). Test pH. Slowly add monoethanolamine ($C_2H_7NO$) until a pH of 10.0 is achieved taking care not to allow the temperature to rise more than a few degrees. Add 1.0 g of the sodium laureth sulfate surfactant Genapol® (manufactured by Hoechst Aktiengesellschaft) and 3.0 g of glycerin.

In a separate glass, allow 3.0 g of Carbopol® 934 NF Polymer (manufactured by Noveon, Inc.) to soak overnight in 42 ml of water.

Vigoroulsy mix the thioglycolic acid and Carbopol® solutions until a homogeneous gel is formed having a pH of between 9.2 and 9.3

Formulation 2

Place a 200 ml glass place in an ice bath and add 49.0 g of distilled water. As before, if iron or other metals commonly found in water, are present or suspected, a sequestrant, such as ethylenediaminetetraacetic (EDTA) acid disodium salt ($C_{10}H_{14}N_2Na_2O_8.2H_2O$) should be added, in a quantity not exceeding a final concentration of 0.5%. Add 10 g of thioglycolic acid ($C_2H_4O_2S$) and mix well. Slowly add 14.0 g monoethanolamine ($C_2H_7NO$) until a pH of 10.0 is achieved taking care not to allow the temperature to rise more than a few degrees. Add 1.0 g of the sodium laureth sulfate surfactant Genapol® (manufactured by Hoechst Aktiengesellschaft) and 3.0 g of glycerin.

In a separate 100 ml glass place 11.0 g cetyl alcohol ($C_{16}H_{34}O$), 3.0 g of glyceryl monostearate ($C_{28}H_{20}O_2$), 3.0 g castor oil and 1.0 g mineral oil.

Finally, heat the glyceril/castor oil solution to approximately 70° C. and mix with the thioglycolic acid solution rapidly cooling the mixture to 40° C.

Final Composition

Having prepared Compounds "A" through "E" the final composition of the Monoethanolamine Salt Product is prepared by combining the entire amount of Compound "E" (Formulation 1 or Formulation 2) with 2.0 g of Compound "A", 1.0 g of Compound "B", 1.0 g of Compound "C" and 1.0 g of Compound "D". If desired, between 3.0 and 5.0 g of methyl salicylate ($C_8H_8O_3$) may be substituted for an equal amount of water to mask odor.

It should be understood that the above amounts and proportion of Compounds "A" through "E" have been determined through experimentation to be most effective but that other amounts and proportions have also been determined to be effective.

II. Oxidizing Agent

The Oxidizing Agent of the present invention is designed to restore disulfuric bonds in the keratin of the treated hair follicles to its condition prior to treatment with the Monoethanolamine Salt Product. Oxidizing agents are well known in the field of hair care and hair treatment. It has been determined through experimentation the preferred composition of the oxidizing agent of the present invention is a solution of sodium bromate (NaBrO₃) in water combined with a stabilizer to allow for ease of application.

The Oxidizing Agent can be prepared in the following fashion: in a 100 ml glass, combine sufficient distilled water (approximately 90–100 g) to dissolve 10 g of sodium bromate (BrNaO₃) and mix well. Add between 0.3% and 0.7% in weight of urea (CH₄N₂O) and mix. The composition can then be prepared into an emulsion or a gel, as preferred, using methods well known in the art.

III. Method of Use

The preferred method of use is different for men and women due to physiological reasons which are not well understood. It has been observed that women generally require less treatment than men.

In a typical treatment, the Monoethanolamine Salt Product is applied topically to the roots of a cleaned scalp using a plastic applicator that allows sufficient precision for this task. The Monoethanolamine Salt Product is left on the scalp for approximately one (1) hour (for men) or 45 minutes (for women) and the scalp is then thoroughly washed with warm water and massaged until none of the product can be felt on the scalp.

Next, the Oxidizing Agent is topically applied to the scalp in the same fashion. The Oxidizing Agent should be allowed to remain on the scalp for 30 minutes or longer (regardless of whether the patient is male or female) and then the scalp should be thoroughly washed with warm water and massaged until none of the agent can be felt on the scalp.

Treatment sessions should be spaced at least 3 months apart. As previously stated, it has been observed that women generally require less treatment than men. Accordingly, the treatment sessions for women can be spaced apart as long as 12 months.

It has been observed through experimentation that in addition to the hair growth effects described above, the compositions of the present invention also have cosmetic effects. Particularly, the compositions of the present invention give hair a thicker, healthier appearance and appear to induce regeneration of the scalp tissue. Moreover, scalp conditions such as dandruff, seborrhea and psoriasis show marked improvement and reduced symptoms as a result of use of the disclosed compounds.

Finally, it should also be pointed out that the above effects of the disclosed invention, including the hair growth and cosmetic effects, have been demonstrated to occur not only in humans but also in many other mammals.

Accordingly, it will be understood that the preferred embodiments of the invention have been disclosed by way of example and that other modifications and alterations may occur to those skilled in the art without departing from the scope and spirit of the appended claims.

What is claimed is:

1. A kit for stimulating hair growth comprising first product and second products wherein:
    said first product comprises an effective amount of monoethanolamine salts and an enzyme, wherein said monoethanolamine salts are present in said first product in the following ranges per weight: 20 to 40 percent is monoethanolamine thioglycolate, 0.1 to 7 percent is monoethanolamine salicylate, .01 to 5 percent is monoethanolamine glycolate, and .01 to 5 percent is monoethanolamine lactate; and
    said second product comprises an effective amount of an oxidizing agent.

2. A kit for stimulating hair growth comprising a separate first product and a separate second product wherein: said separate first product is comprised of 20–40 percent per weight monoethanolamine thioglycolate, 0.1–7 percent per weight monoethanolamine salicylate, 0.1–5 percent per weight monoethanolamine glycolate, 0.1–5 percent per weight monoethanolamine lactate and 0.1–5 percent per weight papain; and said separate second product is comprised of a solution of sodium bromate, water and stabilizer.

3. A method for stimulating hair growth on a human scalp comprising, providing the kit of claim 1 or claim 2, applying the first product to the scalp, removing said first product from the scalp, applying the second product to the scalp, and removing said second product from the scalp.

4. The method of claim 3, wherein the scalp is male, the first product is left on the male scalp for approximately 60 minutes before removing, and the second product is left on the scalp for approximately 30 minutes before removing.

5. The method of claim 4 wherein the steps are repeated at least every three months.

6. The method of claim 3 wherein the scalp is female, the first product is left on the male scalp for approximately 45 minutes before removing, and the second product is left on the scalp for approximately 30 minutes before removing.

7. The method of claim 6 wherein the steps are repeated at least every 6 months.

* * * * *